United States Patent [19]

Sugimoto

[11] Patent Number: 4,621,051

[45] Date of Patent: Nov. 4, 1986

[54] PROCESS FOR THE PRODUCTION OF HUMAN MULTIPLICATION-STIMULATING ACTIVITY

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 585,618

[22] Filed: Mar. 5, 1984

Related U.S. Application Data

[63] Continuation-in-part of Ser. No. 329,119, Dec. 9, 1981, abandoned.

[30] Foreign Application Priority Data

Dec. 31, 1980 [JP] Japan ................ 55-185731

[51] Int. Cl.$^4$ .............. C12P 21/00; C12N 15/00; C12N 5/00; C12N 5/02
[52] U.S. Cl. .................. 435/68; 435/172.2; 435/240; 435/241; 435/284; 435/948; 530/399; 935/106; 935/109
[58] Field of Search ............. 435/1, 6, 172.2, 172.3, 435/240, 241, 68, 948, 248, 284, 286; 436/548; 424/85–87; 260/112 B, 112 R; 935/106, 109; 530/399

[56] References Cited

U.S. PATENT DOCUMENTS

| | | | |
|---|---|---|---|
| 3,935,066 | 1/1976 | Apostolov | 435/240 |
| 4,242,460 | 12/1980 | Chick et al. | 435/284 |
| 4,276,282 | 6/1981 | Sugimoto et al. | 424/85 |
| 4,285,929 | 8/1981 | Sugimoto et al. | 424/85 |
| 4,328,207 | 5/1982 | Sugimoto | 424/85 |
| 4,377,513 | 3/1983 | Sugimoto et al. | 260/112 R |
| 4,383,034 | 5/1983 | Sugimoto | 435/70 |
| 4,383,035 | 5/1983 | Sugimoto | 435/70 |
| 4,383,036 | 5/1983 | Sugimoto | 435/70 |

OTHER PUBLICATIONS

Pontecorvo, G., "Production of Mammalian Somatic Cell Hybrids by Means of Polyethylene Glycol Treatment", *Somatic Cell Genetics*, vol. 1, No. 4, pp. 397–400 (1975).

Yamanaka, T. et al, "Cultivation of Fused Cells Resulting from Treatment of Cells with HVJ", *Biken Journal*, vol. 9, 159–175 (1966).

Peterson, J. A. et al, "Expression of Differentiated Functions in Hepatoma Cell Hybrids; Induction of Mouse Albumin Production in Rat Hepatoma-Mouse Fibroblast Hybrids", *Proc. Nat. Acad. Sci. U.S.A.*, vol. 60, #3, 571–575 (1972).

Malawista, S. E. et al, "Expression of Differentiated Functions in Hepatoma Cell Hybrids: High Frequency of Induction of Mouse Albumin Production in Rat Hepatoma-Mouse Lymphoblast Hybrids", *Proc. Nat. Acad. Sci. U.S.A.*, vol. 71, #3, 927–931 (1974).

Nissley, S. P. et al, "Multiplication-Stimulating Activity (MSA): A Somatomedin-like Polypeptide from Cultured Rat Liver Cells", *Nat. Cancer Institute Monograph*, No. 48, Third Decennial Review Conference, pp. 167–177.

Thompson; J. S. et al, "Heterologous Transplantation of Mouse Tumors into the Newborn Albino Rat", *Cancer Research*, vol. 20, pp. 1365–1371 (1960).

Zeleznik, *Endocrinology*, 1979, vol. 105, pp. 156–162.

Pattillo, Hormone Synthesis and Function, in vitro, *Growth, Nutrition and Metabolism of Cells in Culture*, 1972, Academic Press, N.Y., 225–227.

Bordelon et al,; Human Glycoprotein Hormone Production in Human-Human and Human-Mouse Somatic Cell Hybrids, *Chem. Abs.*, vol. 86, p. 53093.

Lewin, *Gene Expression*, 1980, Wiley and Sons, N.Y., pp. 259–265.

Bordelon, M. R., et al, Exp. Cell Research, vol. 103, 303–310, (1976).

Owerbach et al, Science, vol. 209, 289–292, Jul. 1980.

*Primary Examiner*—Sidney Marantz
*Assistant Examiner*—Patricia L. DeSantis
*Attorney, Agent, or Firm*—Browdy and Neimark

[57] ABSTRACT

The present invention relates to a process for the production of human Multiplication-Stimulating Activity (hMSA).

More precisely, the invention relates to a process for the mass production of low-cost hMSA, comprising in vivo multiplication of human cells capable of producing said substance, and subsequent in vitro production of hMSA with the multiplied human cells.

hMSA production according to the present invention is much higher, about 2–50-fold higher in terms of hMSA production per cell, than that attained by conventional processes: thus, hMSA can be used in a sufficient amount in the prevention and treatment of human diseases.

21 Claims, No Drawings

PROCESS FOR THE PRODUCTION OF HUMAN MULTIPLICATION-STIMULATING ACTIVITY

The present application is a continuation-in-part of parent application Ser. No. 329,119, filed Dec. 9, 1981, abandoned, the entire contents of which are hereby incorporated by reference.

DETAILED DESCRIPTION OF THE INVENTION

The present invention relates to a process for the production of human Multiplication-Stimulating Activity (hereinafter referred to as "hMSA").

As reported in Nissley, S. P. and Rechler, M. M., *National Cancer Institute Monograph*, No. 48, pp. 167–177 (1978), multiplication-stimulating factor (MSA) is a hormone-like peptide which resembles the somatomedins found in human plasma. Its effect is growth hormone dependent and it is active on various tissues. It is also known that MSA stimulates the DNA synthesis and multiplication of the cells of various tissues, promotes the oxidation of glucose in fat cells, and, when administered in vivo, causes a reduction in the blood sugar level, which is recognized as an insulin-like action. MSA shares with the somatomedins the following additional physiochemical properties: a molecular weight of 5,000–10,000 daltons, and heat and acid stability. Although the mode of action of MSA is yet to be fully known, it is clear that its action may be closely related with metabolic phenomena such as regeneration and multiplication of the cells.

The commercialization of MSA, as a drug, has been in great expectation for many years; however, conventional processes for MSA production, such as those involving in vitro culture of rat liver cells, are ineffective to produce sufficient amounts of MSA for clinical and therapeutic uses. Furthermore, while MSA of rat liver origin is substantially non-species-specific, it is less desirable to use such MSA of animal origin as opposed to the corresponding MSA of human origin, i.e. hMSA. There is a particular risk as to antigen-antibody reaction of the MSA derived from animal when used as therapeutic agents for humans, as opposed to hMSA.

The present inventor has investigated processes for mass production of homogenous hMSA. The efforts have resulted in the unexpected finding that human cells obtained by multiplying human cells capable of producing hMSA, using non-human warm-blooded animals, have much higher producibility than that of cells grown solely by in vitro tissue culture: up to about 2 to 50-fold of the latter in terms of hMSA production per cell.

More precisely, the present invention relates to a process for the production of hMSA, characterized in multiplying human cells capable of producing hMSA by transplanting the cells to a non-human warm-blooded animal body, or alternatively multiplying the cells by allowing the cells to multiply with a device by which the nutrient body fluid of a non-human warm-blooded animal is supplied to the cells, and allowing the cells obtained by either of the above multiplication procedures to release hMSA.

The process according to the present invention, besides realizing a greater hMSA production, requires no or much less nutrient medium containing expensive serum for cell multiplication, and renders the maintenance of the culture medium during the cell multiplication much easier than in the case of in vitro tissue culture. Particularly, any human cells capable of producing hMSA can be multiplied easily while utilizing the nutrient body fluid supplied from non-human warm-blooded animals by transplanting the cells in to the animal, or suspending the cells in a diffusion chamber devised to receive nutrient body fluid from the animal body, and feeding the animal in the usual way. In addition, the process is characterized by stabler and higher cell multiplication, and higher hMSA production per cell than any conventional processes for cell multiplication.

As to the cells usable in the present invention, any cells can be used so far as they produce hMSA and multiply easily in a non-human warm-blooded animal body. For example, human cells which inherently produce hMSA, such as human liver cells, those transformed by virus, carcinogenic agent or radiation, and human liver carcinoma cells from a patient with liver carcinoma; human lung carcinoma cells which produce ectopic hMSA; and established cell lines of the above cells, are feasible in the present invention. Also, the use of easily maintainable established human lymphoblastoid lines into which have been introduced hMSA production-coding genetic sites by means of genetic recombination techniques using enzymes such as DNA ligase, nuclease and DNA polymerase, or by cell fusion, results advantageously in a remarkably higher cell multiplication when the cells are transplanted to a non-human warm-blooded animal body, and in an about two to ten-fold higher hMSA production per cell.

References which disclose methods of cell fusion include Yamanaka, T. et al, *Biken Journal*, vol. 9, pp. 159–175 (1966), or Pontecorvo, G., *Somatic Cell Genet.*, vol. 1, No. 4, pp. 397–400 (Oct. 1975), the contents of which are hereby incorporated by reference. The cell fusion inducing agent which may be used in this process may be any agent which will induce cell fusion, preferably Sendai virus or polyethylene glycol.

Furthermore, since transplantation of the above mentioned established human lymphoblastoid lines to the animal body results in the formation of massive tumors, and said massive tumors are hardly contaminated with the host animal cell and disaggregated easily, the multiplied viable human lymphoblastoid cells can be harvested easily.

Human lymphoblastoid lines into which hMSH production ability may be introduced are obtainable by establishing in a suitable manner human lymphoblastoid cells from a patient suffering from a leukemia, e.g. acute lymphatic leukemia, chronic myelogenous leukemia, or acute myelogenous leukemia, malignant lymphoma, Burkitt lymphoma, or infectious mononucleosis. Human lymphoblastoid lines usable may be obtained by transforming normal human lymphocytes by use of a suitable carcinogenic virus, agent or irradiation, such as Epstein-Barr virus (EB virus), mitogen or x-ray irradiation, and establishing the obtained lymphoblastoid cells. Examples of such lines are B-Ta, Q-Ta, B-Ue, Q-Ue, B-Ke, and Q-Ku, reported in *Protein, Nucelic Acid and Enzyme*, vol. 20, No. 6, pp. 616–643 (1975). Preferably, the human lymphoblastoid line is of leukemic origin as, for example, Namalva, reported by Strander, H. et al, *Journal of Microbiology*, vol. 1, pp. 116–117 (1975), BALL-1, TALL-1, and NALL-1, reported by Miyoshi, I. et al, *Nature*, vol. 267, No. 4614, pp. 843–844 (1977), or JBL reported by Miyoshi, I. et al, *Cancer*, vol. 40, pp. 2999–3003 (1977). Other lymphoblastoid cell lines usable include the other human lymphoblastoid cell lines listed in the above cited Strander et al publication, including Akuba, P3HR-1, and LY-46. Others include the cell lines of M-7002 and B-7101 as described in *Journal of Immunology*, vol. 113, pp. 1334–1345 (1974); EBV-SA, EBV-Wa, MOLT-3 and EBV-HO, as described in *The Tissue Culture*, vol. 6, No. 3, pp. 527–546 (1980); CCRF-SB (ATCC CCL120); BALM 2; DND-41; etc.

As to the animals usable in the present invention, any animal can be used according to the present invention so far as the cells multiply therein. For example, poultry, such as chicken and pigeon, or a mammalian, such as dog, cat, monkey, goat, pig, cow, horse, rabbit, guinea pig, rat, hamster, mouse and nude mouse, is advantageously usable in the present invention.

Since such cell transplantation elicits undesirable immunoreaction, the use of a newborn or infant animal, or those in the youngest possible stage, for example, egg, embryo or foetus is desirable.

In order to reduce the immunoreaction, the animal may be treated, prior to the cell transplantation, with irradiation of about 200 to 600 rem of X-ray or $\gamma$-ray, or with injection of antiserum or immunosuppressive agent prepared according to conventional methods. Since nude mice, used as the non-human warm-blooded animal, exhibit weaker immunoreaction even in their adulthood, any established human cells can be transplanted and multiplied rapidly therein without such pretreatment.

Stabilization of the human cell multiplication and augmentation of hMSA production can both be attained by repeated cell transplantation procedures using combination(s) of different non-human warm-blooded animals; for example, the human cells may be implanted and multiplied firstly in hamster, then the multiplied cells can be reimplanted in another animal, for example, nude mouse. Furthermore, the repeated cell transplantation as described above can be carried out effectively with animals of the same class or division as well as with those of the same species or genus.

As to where the human cells are implantable in the host animal body, the human cells can be implanted in any site of the animal so far as the cells multiply therein. For example, the cells are implantable in the allantoic cavity, or intravenously, intraperitoneally or subcutaneously.

Besides direct cell transplantation of the cells to the animal body, any of conventional established human cell lines capable of producing hMSA can be multiplied while utilizing the nutrient body fluid supplied from the animal body by embedding, for example, intraperitoneally, in the animal body a conventional diffusion chamber, of any of various shapes and sizes, and equipped with a porous membrane filter, ultra filter or hollow fiber with pore sizes of about $10^{-7}$ to $10^{-5}$ m in diameter, which prevents contamination of the diffusion chamber with host cells and allows the animal to supply its nutrient body fluid to the cells. Additionally, the diffusion chamber can be designed, if necessary, so it could be placed, for example, on the host animal, and the body fluid allowed to circulate from the animal body into the chamber, to enable observation of the cell suspension in the chamber through transparent side window(s) equipped on the chamber wall(s), and to enable replacement and exchange with a fresh chamber; cell multiplication thereby increases to a further higher level over the period of the animal life and the human cell production per animal is further augmented without sacrificing the host animal.

Furthermore, when such diffusion chamber is used, since the multiplied human cells can be harvested easily and no immunoreaction is elicited due to the absence of direct contact of human cells with the host animal cells, any non-human warm-blooded animal can be used as the host in the present invention without any pretreatment to reduce the immunoreaction.

Feeding of the host animal implanted with the human cells can be carried out easily by conventional methods, and no special care is required even after the cell transplantation.

The period required to obtain the maximum cell multiplication in the host animal body is usually one to 20 weeks. However, when an established human lymphoblastoid cell line or tumor cell line is implanted in the host animal, the maximum cell multiplication of such established cell line can be attained within one to five weeks after the cell transplantation due to their much higher cell multiplication rates.

According to the present invention, the number of human cells obtained per host animal is about $10^7$ to $10^{12}$ or more. In other words, the number of human cells transplanted in the animal body increases about $10^2$ to $10^7$-fold or more, corresponding to about 10 to $10^6$-fold or more than that attained by in vitro tissue culture method using nutrient medium; thus, the human cells are conveniently usable for hMSA production.

As to the method for release of hMSA from the multiplied human cells, any method can be employed so far as the human cells obtained by the above mentioned procedure release hMSA thereby. For example, the multiplied human cells, obtained by multiplying the cells in ascite in suspension and harvesting them from said ascite, or by extracting the massive tumor formed subcutaneously and harvesting it after disaggregation of said massive tumor, are suspended in a concentration of about $10^4$ to $10^8$ cells per ml in a nutrient medium, kept at a temperature of about 20° to 40° C., and then incubated at this temperature for about one to a few weeks to release hMSA. During the incubation period, the nutrient medium, if necessary, can be replaced with a fresh preparation of the same medium, at regular intervals to supply sufficient nutrients to the cells, and the hMSA released in the used medium can also be harvested.

The hMSA thus obtained can be collected easily by purification and separation using conventional techniques such as salting-out, dialysis, filtration, centrifugation, concentration and lyophilization. If a further purified hMSA is desirable, a hMSA preparation with the highest purity can be obtained by the above mentioned techniques in combination with conventional techniques such as adsorption and desorption with ion exchamge, fractionation by molecular weight, affinity chromatography, isoelectric point fractionation and electrophoresis.

The hMSA preparation thus obtained is immunologically and physiochemically identical with those obtained by conventional methods, and has a potent efficacy. The hMSA preparation is advantageously usable alone or in combination with one or more agents for injection, external, internal, or diagnostical administration in the prevention and treatment of human diseases.

The hMSA in the culture medium was determined according to the assay method as described in Norman C. Dulak and Howard M. Tennis, Journal of Cellular Physiology, Vol. 81, pp. 161–170 (1973). As described in the above report, one unit of hMSA is defined as that amount of activity causing stimulation of 3H-thymidine incorporation equivalent to that caused by 1 mg of whole calf serum protein.

Several embodiments of the present invention are disclosed in detail hereinafter. Of course, this description is made only by way of example and not as a limitation on the scope of the invention.

EXAMPLE 1

Minced and disaggregated human liver carcinoma cells, obtained by extracting from a patient with liver carcinoma, were implanted subcutaneously in adult nude mice which were then fed in the usual way for four weeks. The resultant massive tumors, about 9 grams each, were minced and suspended in a saline solution containing trypsin to disaggregate the massive tumors. After washing the cells with serum-free RPMI 1640 medium (pH 7.2), the cells were resuspended in a fresh preparation of the same medium to give a cell concentration of about $10^5$ cells per ml, and incubated therein at 37° C. for 15 days to release hMSA while replacing periodically the medium with fresh medium. The used medium was frozen at $-20°$ C. immediately after the replacement and stored until later use. After the incubation period, the supernatant of the cell suspension and the medium prepared from the frozen stock by thawing were centrifuged together at about 8,000 rpm for 30 minutes and the supernatant thus obtained was assayed for its hMSA. The hMSA production was about 7,500 units per ml of the cell suspension.

Control cells, obtained by cultivating in vitro the same cells, human liver carcinoma cells, in Eagle's medium (pH 7.2), supplemented with 1 v/v% foetal bovine serum and 20 v/v% broth, and incubating at 37° C., were treated similarly as above to release hMSA. The hMSA production was only about 25 units per ml of the suspension.

EXAMPLE 2

Minced and disaggregated human liver carcinoma cells extracted from a patient with liver carcinoma and a human leukemic lymphoblastoid cell line Namalwa were suspended in a vessel with a salt solution containing 140 mM NaCl, 54 mM KCL, 1 mM $NaH_2PO_4$ and 2 mM $CaCl_2$ to give a respective cell concentration of about $10^3$ cells per ml, and the cell suspension was mixed with a fresh preparation of a salt solution with the same composition and containing UV-preinactivated Sendai virus under ice-chilling conditions. Five minutes after the mixing, the mixed suspension was placed in a 37° C. incubator and incubated therein for 30 minutes with agitation to effect cell fusion and introduction of the ability of producing hMSA into the human lymphoblastoid cell line Namalwa. After cloning the hybridoma cell line that is capable of producing hMSA according to conventional methods, the hybridoma cell line was transplanted intraperitoneally into adult nude mice and the nude mice were fed for five weeks in the usual way. The massive tumors, about 14 grams each, were extracted and treated similarly as in EXAMPLE 1 to release hMSA. The hMSA production was about 32,000 units per mol of the cell suspension.

A control test was carried out similarly as in EXAMPLE 1 by cultivating in vitro the fused human lymphoblastoid line Namalwa, and allowing the multiplied cells to release hMSA. The hMSA production was only about 1,100 units per ml of the cell suspension.

EXAMPLE 3

After injection of antiserum, prepared from rabbits according to conventional methods, into newborn hamsters to reduce their possible immunoreaction resulting from cell transplantation, the animals were implanted subcutaneously with a human leukemic lymphoblastoid line JBL wherein the hMSA-producing ability was introduced similarly as in EXAMPLE 2, and the fed in the usual way for three weeks. The resultant massive tumors, about 11 grams each, formed subcutaneously in the hamsters and were extracted and treated similarly as in EXAMPLE 1, except that Eagle's medium (pH 7.2), containing 20 v/v% broth was employed as a nutrient medium for the incubation instead of RPMI 1640 medium, to release hMSA. The hMSA production was about 45,000 units per ml of the cell suspension.

A control test was carried out similarly as in EXAMPLE 1 by cultivating in vitro the fused human leukemic lymphoblastoid line JBL, and allowing the multiplied cells to release hMSA. The hMSA production was only about 2,100 units per ml of the cell suspension.

EXAMPLE 4

Newborn rats were implanted intravenously with a human leukemic lymphoblastoid line BALL-1 wherein the the ability of the producing hMSA was introduced similarly as in EXAMPLE 2, and then fed in the usual way for four weeks. The resultant massive tumors, about 38 g each, were extracted and treated similarly as in EXAMPLE 1 to release hMSA. The hMSA production was about 42,000 units per ml of the cell suspension.

A control experiment was carried out by cultivating in vitro the fused human leukemic lymphoblastoid cell line BALL-1, and allowing the multiplied cells to release hMSA. The hMSA production was only about 1,900 units per ml of the cell suspension.

EXAMPLE 5

After adult mice were irradiated with about 400 rem of X-ray to reduce their immunoreaction, they were implanted subcutaneously with human hepatoma cells, obtained similarly as in the EXAMPLE 1, and fed in usual way for four weeks. The resultant massive tumors, about 15 g each, formed subcutaneously in the mice, were extracted and treated similarly as in EXAMPLE 3 to release hMSA. The hMSA production was about 9,600 units per ml of the cell suspension.

A control test was carried out by cultivating in vitro the human liver carcinoma cells, and allowing the multiplied cells to release hMSA. The hMSA production was only about 280 units per ml of the suspension.

EXAMPLE 6

A human leukemic lymphoblastoid line JBL, wherein the hMSA producing ability was introduced similarly as in EXAMPLE 3, was suspended in physiological saline solution and transferred into a cylindrical plastic diffusion chamber, with an inner volume of about 10 ml, and equipped with a membrane filter, having pore sizes of about $0.5\mu$ in diameter, and the chamber was embedded intraperitoneally in an adult rat. After feeding the rat for four weeks in the usual way, the chamber was removed. The human cell density in the chamber attained by the above operation was about $2 \times 10^9$ cells per ml which was about $10^3$-fold, or more, higher than that attained by in vitro cultivation using a $CO_2$ incubator. The cells thus obtained were treated similarly as in EXAMPLE 3 to release hMSA. The hMSA production was about 57,000 units per ml of the cell suspension.

EXAMPLE 7

A human leukemic lymphoblastoid line BALL-1 wherein the hMSA-producing ability was introduced similarly as in EXAMPLE 4 was implanted in allantoic cavities of embryonatd eggs which had been preincubated at 37° C. for five days. After incubation of the eggs at this temparature for an additional one week, the multiplied human cells were harvested. The cells were treated similarly as in EXAMPLE 1 to release hMSA. The hMSA production was about 35,000 units per ml of the cell suspension.

It will be obvious to those skilled in the art that various changes may be made without departing from the scope of the invention and the invention is not to be considered limited to what is described in the specification.

What we claim is:

1. A process for producing human multiplication-stimulating activity (hMSA), comprising:
   implanting human tumor forming cells capable of producing hMSA in a non-human warm-blooded animal;
   feeding the animal to allow said human cells to utilize the nutrient body fluid of the animal for their multiplication;
   extracting and disaggregating the resultant tumor, formed in the animal, to obtain the multiplied human cells;
   culturing the multiplied human cells on a culture medium under conditions appropriate to accumulate a substantial amount of hMSA; and
   recovering the accumulated hMSA from the culture.

2. A process in accordance with claim 1, wherein said human cells capable of producing hMSA are human liver carcinoma cells.

3. A process in accordance with claim 1, wherein said human cells capable of producing hMSA are human lung carcinoma cells.

4. A process in accordance with claim 1, wherein said human cells capable of producing hMSA are hybridoma cells.

5. A process in accordance with claim 1, wherein said non-human warm-blooded animal is a fowl or a mammalian.

6. A process in accordance with claim 1, wherein said non-human warm-blooded animal is a member selected from the group consisting of chicken, pigeon, dog, cat, monkey, goat, pig, cow, horse, guinea pig, rabbit, rat, hamster, nude mouse and mouse.

7. A process in accordance with claim 1, wherein said human cells capable of producing hMSA are hybridoma cells obtained by:
   suspending hMSA-producing human cells together with human lymphoblastoid cells in a salt solution containing an effective amount of a cell fusion inducing agent;
   allowing the resultant cell suspension to stand for a period sufficient to effect cell fusion; and
   selecting or cloning hybridoma cells which produce hMSA.

8. A process in accordance with claim 7, wherein said human lymphoblastoid cells are of leukemic origin.

9. A process in accordance with claim 7, wherein said human lymphoblastoid cells are selected from the group consisting of Namalva, JBL, BALL-1, NALL-1 and TALL-1 cells.

10. A process in accordance with claim 7, wherein said cell fusion inducing agent is an inactivated Sendai virus or polyethylene glycol.

11. A process for producing human multiplication stimulating activity (hMSA), comprising:
    suspending human tumor forming cells capable of producing hMSA in a device in which the nutrient body fluid of a non-human warm-blooded animal can be supplied to said human cells;
    embedding or placing said device in or on a non-human warm-blooded animal in a manner such that the nutrient body fluid of said animal is supplied to the human cells within said device;
    feeding said animal to allow said human cells to utilize the nutrient body fluid for their multiplication;
    harvesting the multiplied human cells from the device;
    culturing the multiplied human cells on a culture medium under conditions appropriate to accumulate a substantial amount of hMSA; and
    recovering the accumulated hMSA from the culture.

12. A process in accordance with claim 11, wherein said human cells capable of producing hMSA are human liver carcinoma cells.

13. A process in accordance with claim 11, wherein said human cells capable of producing hMSA are human lung carcinoma cells.

14. A process in accordance with claim 11, wherein said human cells capable of producing hMSA are hybridoma cells.

15. A process in accordance with claim 11, wherein said non-human warm-blooded animal is a fowl or a mammalian.

16. A process in accordance with claim 11, wherein said non-human warm-blooded animal is a member selected from the group consisting of chicken, pigeon, dog, cat, monkey, goat, pig, cow, horse, guinea pig, rabbit, rat, hamster, nude mouse and mouse.

17. A process according to claim 11, wherein said device is a diffusion chamber equipped with a membrane filter, ultra filter or hollow fiber having a nominal pore size in the range of $10^{-7} - 10^{-5}$ m.

18. A process in accordance with claim 11, wherein said human cells capable of producing hMSA are hybridoma cells obtained by:
    suspending hMSA-producing human cells together with human lymphoblastoid cells in a salt solution containing an effective amount of a cell fusion inducing agent;
    allowing the resultant cell suspension to stand for a period sufficient to effect cell fusion; and
    selecting or cloning hybridoma cells which produce hMSA.

19. A process in accordance with claim 18 wherein said human lymphoblastoid cells are of leukemic origin.

20. A process in accordance with claim 18, wherein said human lymphoblastoid cells are selected from the group consisting of Namalva, JBL, BALL-1, NALL-1 and TALL-1 cells.

21. A process in accordance with claim 18, wherein said cell fusion inducing agent is an inactivated Sendai virus or polyethylene glycol.

* * * * *